United States Patent [19]
Plassche, Jr.

[11] Patent Number: 5,308,318
[45] Date of Patent: May 3, 1994

[54] EASY-EXCHANGE DRAINAGE CATHETER SYSTEM WITH INTEGRAL OBTURATOR CHANNEL

[76] Inventor: Walter M. Plassche, Jr., 1209 Clover St., Eochester, N.Y. 14610

[21] Appl. No.: 59,142

[22] Filed: May 7, 1993

[51] Int. Cl.⁵ .......................................... A61M 31/00
[52] U.S. Cl. ..................................... 604/54; 604/165
[58] Field of Search ................... 604/49, 54, 95, 164, 604/165, 169, 280

[56] References Cited

U.S. PATENT DOCUMENTS 5,078,701  1/1992  Grassi et al. ........................... 604/54

Primary Examiner—Jerome L. Kruter
Attorney, Agent, or Firm—M. Lukacher

[57] ABSTRACT

A drainage catheter system, for draining fluids from body organs such as a kidney or a liver in patients whose natural drainage pathways are blocked, has a main drainage lumen and an obturator channel which may be integral with each other. This system can be easily exchanged for a new catheter system when the main drainage lumen of the initially placed catheter system becomes obstructed or occluded by encrusted deposits or tumor ingrowth. Catheter system exchange is initiated by withdrawal of a pre-installed obturator from the obturator channel of the catheter systems. Obturator withdrawal can be used to actuate release of a catheter loop-retaining thread or drawstring from its loop-retaining state in catheter systems which have pigtail loops. Once the obturator has been completely removed, a conventional flexible-tip guidewire is inserted through the now open or un-obturated, obturator channel. The occluded drainage catheter system is removed over the guidewire, a new (exchange) drainage catheter system is positioned by advancing its main drainage lumen along the guidewire, and the guidewire is removed from the new system. Loop formation and loop retention (for looped catheters), and body-external connection to a suitable drainage collector conclude the exchange of drainage catheter systems.

19 Claims, 7 Drawing Sheets

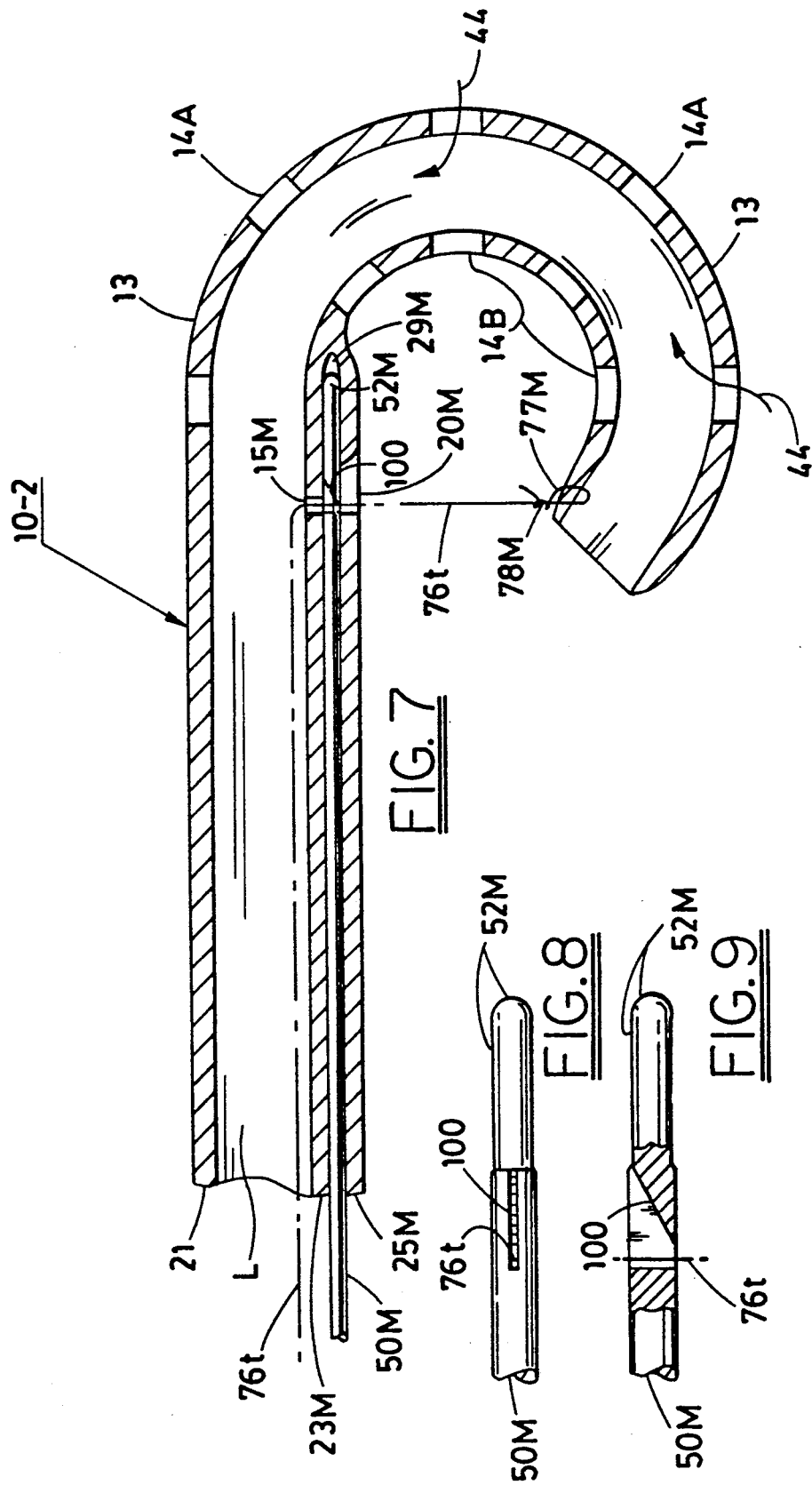

EASY-EXCHANGE DRAINAGE CATHETER SYSTEM WITH INTEGRAL OBTURATOR CHANNEL

FIELD OF THE INVENTION

The present invention relates to medical instruments used for draining liquid such as viscous liquids from body organs in which the liquids are produced, such as a kidney or a liver, or from abscesses, in patients whose natural drainage pathways (ureter for kidney; biliary ductal system for liver) are blocked to an extent which interferes with drainage. More particularly, the invention relates to drainage catheter systems which can be easily exchanged when such drainage catheters become obstructed or occluded by encrusted deposits.

The invention provides an improved catheter system (methods and apparatus) which allows catheter exchange. Exchange is initiated by withdrawal of an obturator from an obturator channel of the catheter system and which may be an integral part thereof. A guidewire is inserted through the now open obturator channel. The exchange is completed by removal of the obstructed drainage catheter system, insertion of a new drainage catheter system over the guidewire, and removal of the guidewire.

BACKGROUND AND FEATURES OF THE INVENTION

Various procedures have been described for the exchange of obstructed drainage catheters while maintaining access between the organ to be drained and the patient's skin surface through the original percutaneous tract, i.e., the original pathway of the very first drainage catheter installed in the patient. Descriptions of such prior art drainage catheters, and particularly descriptions of special methods and equipment developed for exchange of obstructed or occluded drainage catheters, indicate the frequent complexity of such exchange procedures and their attendant treatment times, likely patient discomfort and relative risk factors.

Representative descriptions of drainage catheter exchange procedures can be found in the following publications:

1) Use of flexible, 22-gauge Trocar Needle and an Obturator for Obstructed Drainage Catheter Exchange; G. L. McLellan; American Journal of Radiology, 151: 521–522; September 1988.
2) Exchange of Occluded Catheters with Transcatheter and Pericatheter Maneuvers; A. S. Lee, E. van Sonnenberg, G. R. Wittich, G. Casola; Radiology, 163: 273–274; April 1987.
3) Replacement of Obstructed Loop and Pigtail Nephrostomy and Biliary Drains; C. Cope; American Journal of Radiology, 139: 1022–1023; November 1982.
4) Exchange of an Obstructed Loop Nephrostomy Catheter; F. C. Cazenave, M. C. Glass-Royal, K. H. Barth; Cardiovascular and Interventional Radiology, 13: 327–328; 1990.

In contrast to complex drainage catheter exchange procedures of the prior art, the present invention provides improved drainage catheter systems (method and apparatus) for easy exchange by means of a pre-installed obturator in an obturator channel, which may be integral to the catheter system, and which is installed as a part of the catheter system.

Accordingly, it is a feature of the invention to provide a drainage catheter system having at least one main drainage lumen for draining fluid from an organ whose natural drainage pathway is blocked, and having as a component of the catheter system an obturator channel sealed by an obturator which is removed just prior to exchange or replacement of an initially installed and obstructed or occluded drainage catheter system of the present invention by a new drainage catheter system of the present invention.

It is another feature of the invention to provide easy exchange of an obstructed or occluded drainage catheter system through the original percutaneous tract.

It is a further feature of the invention to provide the easy exchange of drainage catheter systems by use of a conventional flexible-tip guidewire.

It is a still further feature of the invention to provide release means associated with the obturator for releasing a drawstring or retaining thread from its catheter loop-retaining position, thereby freeing the catheter loop from retention and readying the drainage catheter system for the exchange procedure.

Briefly described, the present invention provides an easily exchanged drainage catheter system for drainage of fluids from organs such as, for example, a kidney or a liver, or from abscesses. When obstruction or occlusion of the main drainage lumen of the initially installed catheter system requires exchange or replacement, a sealingly fitting obturator is fully withdrawn from an obturator channel integral to the drainage catheter system. In accordance with an aspect of the invention, the obturator as it is withdrawn from the channel, firstly releases a taut drawstring or retaining thread or other retainer of the looped distal end of the drainage catheter. When withdrawn, the obturator provides an open or unobturated channel between the organ to be drained and the outside of the patient's skin surface. A conventional flexible-tip guidewire (of diameter slightly smaller than the diameter of the unobturated channel) is inserted through the open channel, preferably under fluoroscopic monitoring, and is advanced and manipulated so that the flexible tip is guided through the same aperture in the obturator channel which served as the aperture for the obturator, and for the retainer (e.g., the drawstring or loop-retaining thread). Upon completed guidewire advance, the occluded drainage catheter system is withdrawn over the positionally retained guidewire and discarded. An exchange or replacement drainage catheter system (having an obturator pre-installed in its obturator channel) is now inserted by advancing its main drainage lumen along the guidewire until properly positioned, as can be determined by fluoroscopic observation of the distal drainage section of the drainage catheter system within the fluid-collection space of the organ to be drained. The guidewire is withdrawn and the retainer is set. A loop-retaining thread or drawstring retainer is set by being tensioned and clamped so as to form and retain a loop-shaped end section of the drainage catheter system within the fluid-collection space of the organ. A fluid collection bag (or other suitable fluid collection means) is connected by a standard coupling (for example, a so-called Luer Lock) to the main drainage lumen.

BRIEF DESCRIPTION OF THE DRAWINGS

The foregoing and other objects, features and advantages of the invention, as well as presently preferred embodiments thereof, will become more apparent from a reading of the following description when considered in conjunction with the accompanying drawings, in which:

FIG. 7 is a partial cross-sectional side view of a second embodiment of a drainage catheter system in accordance with the present invention, showing an obturator in an integral obturator channel extending only to the onset of the catheter loop-section, wherein the obturator has a cutter means for severing a loop-retaining thread or drawstring.

FIG. 8-is a top view of the cutter means associated with the obturator of FIG. 7.

FIG. 9-is a partial cross-sectional side view of the cutter means associated with the obturator of FIG. 7.

DETAILED DESCRIPTION OF THE PREFERRED EMBODIMENTS

Figure 1:
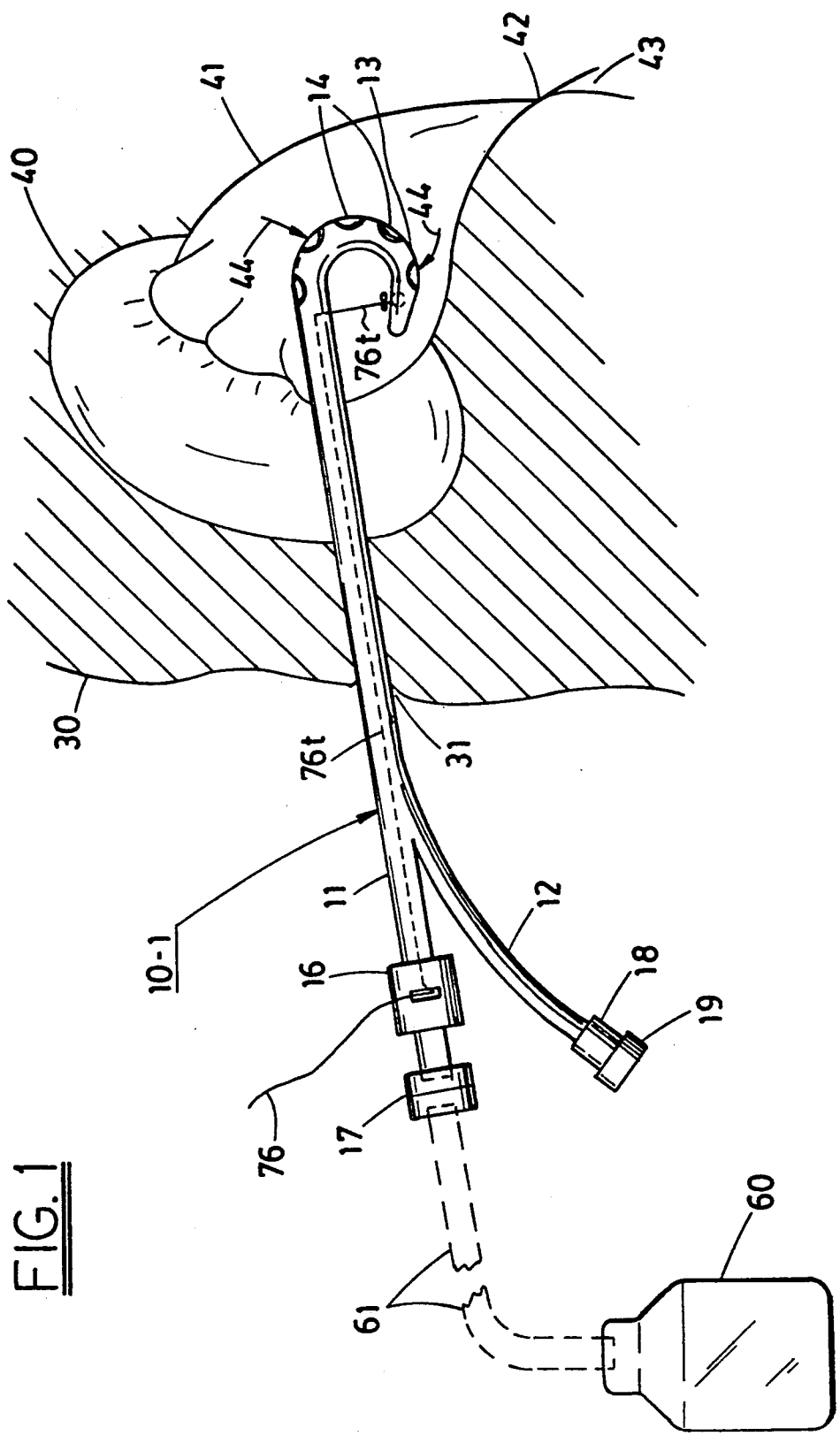
FIG. 1-is a schematic side view of a first embodiment of a drainage catheter system of the present invention, shown with its distal looped end section retained in the fluid-collection space of a kidney, and with a drain tube and associated fluid collection bag connected to the catheter system.
Figure 2:
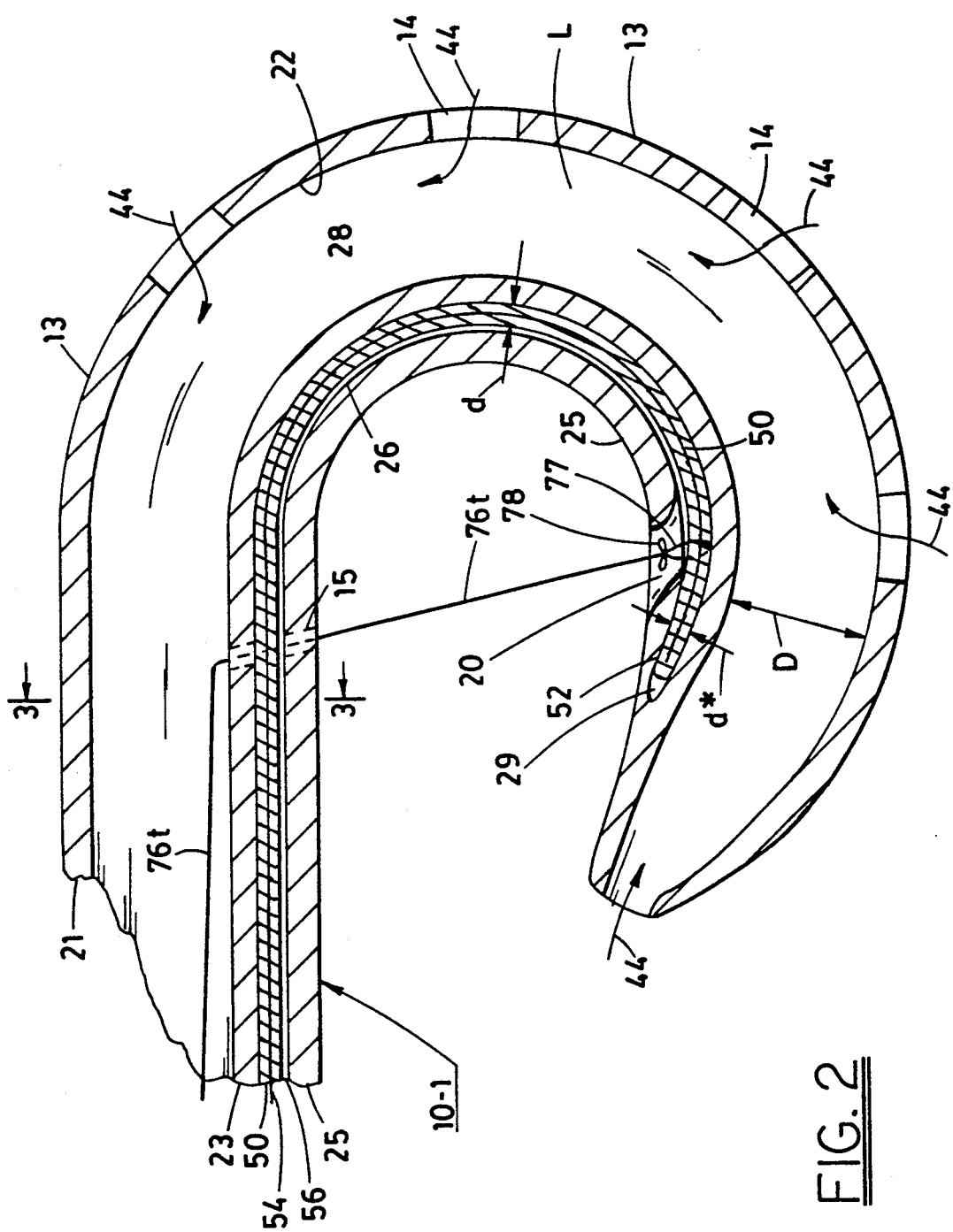
FIG. 2-is an enlarged cross-sectional side view of the distal looped end section of the drainage catheter system of FIG. 1, showing the obturator in the obturator channel and indicating the location of the retaining thread or drawstring near the distal end of the obturator.
Figure 3:
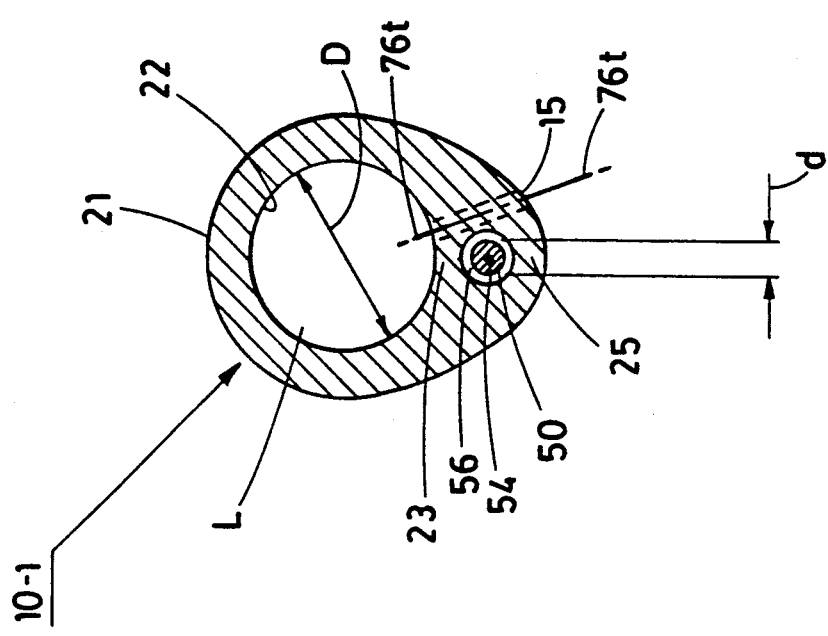
FIG. 3-is an enlarged cross-sectional end view of the drainage catheter system, taken along line 3—3 in FIG. 2.

Referring particularly to FIGS. 1, 2 and 3, there is shown a drainage catheter system 10-1 percutaneously inserted by conventional procedure at 31 along skin surface 30 through a kidney organ 40 into its fluid collection space 41 having blockage 42 of ureter 43. Drainage catheter system 10-1 has a main drainage lumen L of inner diameter D defined by an inner peripheral surface 22 of generally cylindrical catheter wall 21. Integrally within catheter wall regions 23 and 25, and axially coextensive with main lumen L, is an obturator channel 56 containing an obturator 50 which sealingly obturates channel 56 over most of its length, leaving vacant a channel end pocket 29. Obturator channel 56 and obturator 50 are each approximately of diameter d, where $d<<D$. Channel 56 may have a slightly elliptical or oval cross-section to facilitate some sideways motion of obturator 50 in the channel if the entire integral drainage catheter system 10-1 needs to follow a curved pathway in its approach to the organ to be drained of excess fluid. While an obturator channel integral with the lumen is preferred, the obturator channel may be assembled alongside the main lumen in other ways, so long as their installation alongside each other through a single percutaneous opening or tract is effected.

Since drainage catheters are frequently intended to remain positioned within the fluid collection space of an organ to be drained (kidney, liver or abscess) for extended time periods (weeks to months), a curved or looped catheter section 13 is typically formed extending by some distance from the generally conically-shaped distal end of the catheter backwards; the loop (also referred to as a pigtail loop) being confined to within the organ's fluid collection space 41. This loop substantially retains the catheter system 10-1 and its peripheral drain holes 14 in position for extended time periods, so as to permit fluid 44 to enter main drainage lumen L and to be transferred by gravity or by externally applied suction along the lumen through a coupling 17 (for example, a Luer Lock coupling) to a drain line 61 which may be attached to a drain bag 60.

A retainer, such as loop-retaining thread or drawstring 76, is held in a taut condition 76t ("t" is denoting the taut or tensioned condition) within a major section of lumen L by a clamping means 16 (attached to the outside diameter of catheter section 11), thereby retaining the shape of catheter loop 13 by means of thread loop 77 (with knot 78) at the end of thread 76t, the loop slidably surrounding the obturator 50 some distance from its thinned or tapered free end or termination 52 which has a diameter $d^*<d$. Loop-retaining thread 76t runs axially along main lumen L and exits L through a small radial channel 15 toward and into a contoured opening 20 in catheter wall region 25 where obturator 50 retains loop 77. As manufactured, the easy-exchange drainage catheter system is provided with thread or drawstring 76 in a released ("r") condition, and extending from a released clamping means 16 along a major section of lumen L, through the small channel 15 and into contoured opening 20 wherein loop 77 of drawstring 76 is retained by obturator termination 52 of obturator 50. In this pre-insertion configuration, the distal end of the drainage catheter may have a slight curvature to facilitate percutaneous catheter insertion into the organ to be drained.

Obturator 50 is attached at its proximal end to a handle 19, which, in conjunction with a mating part 18, forms a releasable coupling (for example a Luer Lock coupling). From this coupling, obturator 50 projects along a branch 12 of the drainage catheter system 10-1 with substantially uniform diameter d within integral obturator channel 56 until the obturator's thinned or tapered distal end 52 of diameter d* stops its axial advance at the narrowing end pocket portion 29 of channel 56.

To provide obturator 50 with sufficient structural strength in a condition of tension (i.e., when the obturator is withdrawn by pulling on the uncoupled handle 19), an embedded wire 54 is molded or drawn in the approximate center of plastic obturator 50.

The drainage catheter system can be fabricated by conventional processes known in the art, for example, by molding or draw-forming of plastics like polyethylene or polyurethane resins. The obturator is preferably made of Teflon ® and its central wire may be of stainless steel. The loop-retaining thread or drawstring is also of known, non-absorbing material.

Figure 4:
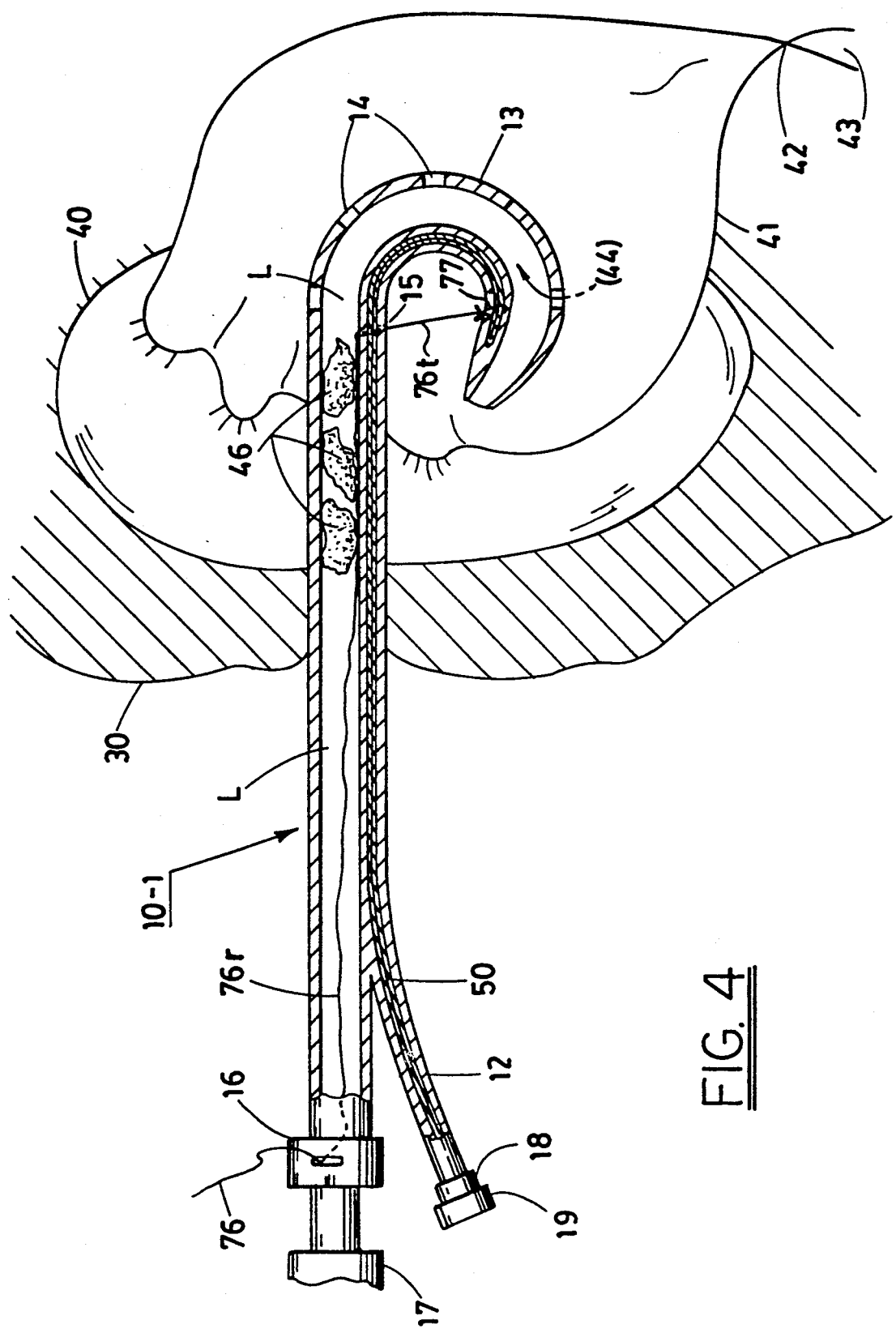
FIG. 4-is a cross-sectional side view of the drainage catheter system of FIGS. 1-3, with the obturator in the obturator channel, and with encrusted particulate deposits blocking the main drainage lumen and preventing the loop-retaining thread from releasing the looped catheter end section.
Figure 5:
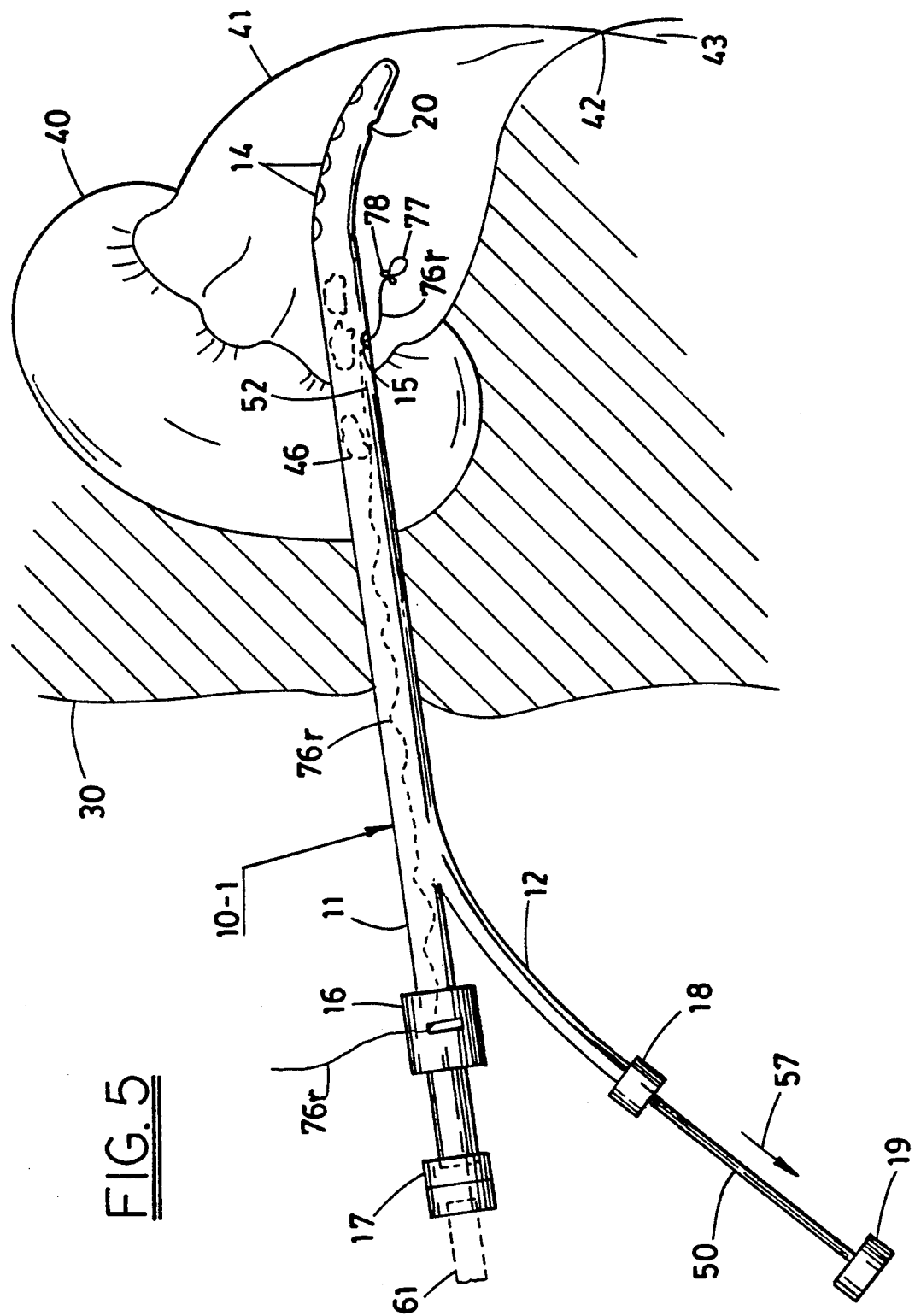
FIG. 5-is a side view of the drainage catheter system of FIGS. 1-3, showing the obturator in the process of being withdrawn from the obturator channel, whereby the obturator withdrawal has released the loop-retaining thread of drawstring from the obturator.
Figure 6:
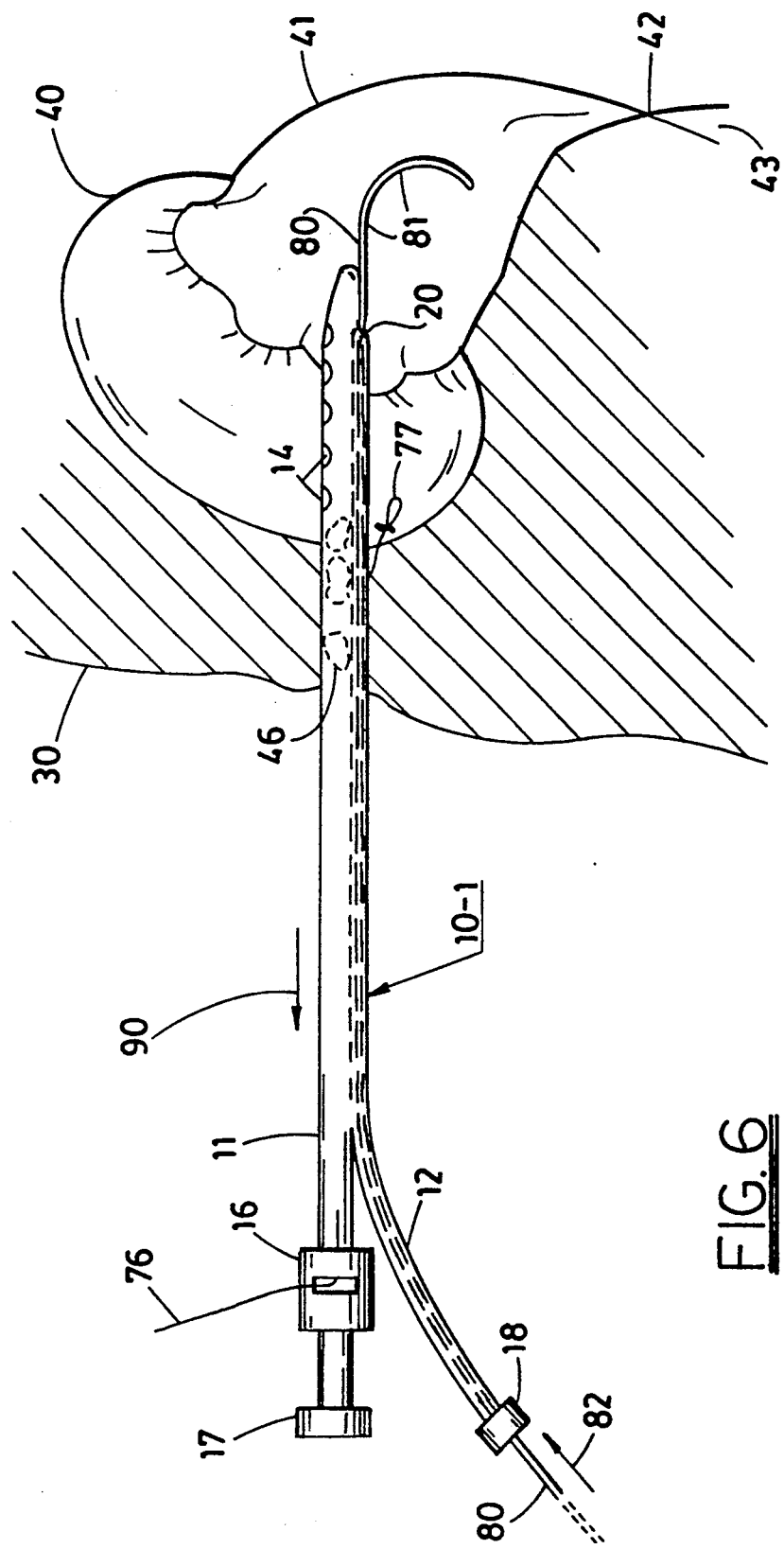
FIG. 6-is a side view of the drainage catheter system of FIGS. 1-3, showing a flexible-tip guidewire inserted into the fluid collection space of a kidney through the unobturated channel prevailing after complete withdrawal of the obturator, and indicating removal of the occluded or obstructed catheter system prior to exchange with a new drainage catheter system having an obturator channel which is integral with the main lumen.

Referring now particularly to FIGS. 4, 5 and 6, there is indicated a sequence of drainage catheter system exchange procedures, necessitated by build-up of encrusted deposits 46 within a portion of main drainage lumen L over an extended period of time during which fluid 44 had been drained from fluid collection space 41. Typically, the virtually complete occlusion or obstruction of lumen L by deposits 46 is indicated by a rapidly decreasing amount of fluid collected in drain bag 60 (see FIG. 1).

As a first procedure in the catheter exchange, the catheter pigtail loop 13 should be loosened by releasing thread or string clamping means 16 whereby thread 76 assumes a released ("r") condition 76r throughout a section of lumen L. However, as shown in FIG. 4, the released or relaxed condition does not propagate beyond encrusted deposits 46, which lock the thread or string in position, thus preventing tension to be released over a section 76t of thread extending from these deposits to loop 77.

In FIG. 5, coupling portion handle 19 has been uncoupled from coupling portion 18, and handle 19 is depicted as having withdrawn obturator 50 through a pulling action 57 by a distance sufficient to slide obturator tip section 52 past aperture 20, thereby releasing loop 77 of drawstring 76 from the obturator (see detail in FIG. 2). Obturator tip 52 is schematically indicated in FIG. 5, as is a loosely dangling thread 76r with its loop 77 and loop knot 78. The drainage catheter tip section is shown to be released into a slightly curved configuration in which drainage catheter system 10-1 can be readily removed. Obturator 50 is now fully withdrawn and discarded.

FIG. 6 shows the remaining drainage catheter system exchange preparation procedures: a conventional guidewire 80 with a flexible tip section 81 is inserted into, and advanced by pushing action 82 through catheter branch 12 along now unobturated channel 56 and through aperture 20 until fluoroscopic monitoring indicates positioning of guidewire tip section 81 in the fluid collection space 41 of kidney 40. The diameter d of obturator channel 56 is selected so as to provide an axially slidable pathway for conventional guidewire 80 and its flexible tip 81 within the obturator channel 56. The diameter d* of the end portion of obturator channel 56 is selected so as to prevent entry of guidewire tip 81 into that end portion, thereby ensuring that the guidewire tip 81 exits the obturator channel 56 through the contoured aperture 20. Guidewire 80 is now held or clamped in place (by a clamp, not shown), and the entire drainage catheter system 10-1 is withdrawn by pulling action 90, through the initial percutaneous opening leaving guidewire tip 81 in its location within space 41. This leaves the initial percutaneous opening (tract) available for insertion of the replacement catheter system, thereby avoiding another invasive procedure to establish a second opening and the associated risk and discomfort to the patient.

The drainage catheter exchange is completed by sliding the main drainage lumen L of a new drainage catheter system with integral obturator channel (with pre-installed obturator and loop-retaining thread or drawstring) over and along guidewire 80 and by advancing the catheter system in the original percutaneous tract under fluoroscopic monitoring until the catheter tip region is properly positioned for pigtail loop formation within fluid collection space 41. Guidewire 80 is now withdrawn and discarded. Connection to drain line 61 (and thus to drainage bag 60) is made at Luer Lock coupling 17, and catheter loop 13 is formed and retained by tensioning loop-retaining thread 76 and clamping it in its tensioned ("t") state at clamping means 16, thereby providing the fluid-drainage condition depicted in FIG. 1.

By the above-described sequence of procedures, exchange of an occluded or obstructed drainage catheter system 10-1 can take place relatively easily and quickly and with minimal risk and discomfort to the patient.

Referring now to FIGS. 7, 8 and 9, there is shown a second embodiment of an easy-exchange drainage catheter system 10-2 with an integral obturator channel, in accordance with the present invention. Catheter system 10-2 differs from catheter system 10-1 (for comparison, see particularly FIG. 2) by the modifications (M) indicated in the designations of parts or functions.

Integral obturator 50M terminates at obturator tip 52M just ahead of obturator channel pocket 29M, at or near the onset of catheter loop 13. Stated differently, obturator 50M does not extend around catheter loop 13. Accordingly, a different release means for taut catheter loop-retaining thread 76t is provided in the second embodiment of the system 10-2 to ensure release of catheter loop 13 upon initiation of catheter exchange procedures by withdrawal of obturator 50M: As indicated schematically in FIG. 7, loop-retaining thread 76t projects upwardly from a permanent attachment 77M, 78M near the end of catheter loop 13 through a shaped aperture 20M in catheter wall 25M into a channel 15M extending through catheter wall section 23M into catheter main lumen L. Thread 76t also passes through obturator 50M in proximity to a cutter provided by a cutting edge or cutting surface 100 which is an integral component of obturator 50M, as indicated particularly in FIGS. 8 and 9. Thus, catheter loop-retaining thread or drawstring 76t is cut by obturator cutting edge 100 as the obturator is withdrawn from the obturator channel in preparation for catheter exchange, thereby releasing the catheter loop 13 from its looped state for subsequent catheter withdrawal.

Another feature of the system 10-2 (which has been omitted from embodiment 10-1 for the sake of clarity of presentation) are catheter drain holes 14B along the inner surface of catheter loop 13, in addition to drain holes 14A along the outer surface of loop 13. All other features and functions, as well as catheter exchange procedures, are common to both embodiments of the invention.

From the foregoing description it will be apparent that an easy-exchange drainage catheter system has been provided which deploys an integral obturator channel and an obturator inserted therein. Variations and modifications of the drainage catheter systems illustrated herein, within the scope of the invention will undoubtedly suggest themselves to those skilled in this art. For example, a so-called dual-lumen sump drainage catheter may be fabricated with one integral obturator for use in some applications where air circulation or flushing or aspiration effects are desirably provided by a second lumen. Also, so-called Malecot drainage catheters may be constructed with an integral obturator channel and obturator for release of suitable retaining thread loop and for easy catheter exchange. Accordingly, the foregoing description should be taken as illustrative and not in a limiting sense.

I claim:

1. A method of easy exchange of an occluded percutaneous drainage catheter system along a tract into a fluid collection space of a patient's body region to be drained through a main drainage lumen and having an obturator in an obturator channel, the method comprising the steps of:
   inserting a non-occluded drainage catheter to remove body fluid;
   withdrawing the obturator from the obturator channel, thereby providing an unobturated channel;
   inserting a guidewire slidably through the unobturated channel into the fluid collection space of the body region;
   holding the guidewire in its inserted position;
   removing the drainage catheter system along the held guidewire when the catheter is occluded;
   introducing an exchange drainage catheter system with the lumen passing over and along the guidewire along the same tract into the fluid collection space of the region; and
   pulling the guidewire from the exchange catheter system.

2. The method according to claim 1 wherein the catheter system has a looped end section and a flexible retainer for retaining the end section in looped condition when tensioned, said retainer extending through said obturator channel and further comprising the steps of actuating the release of said retainer from its loop-retaining condition while providing the unobturated channel, and after the exchange catheter system is introduced, tensioning and clamping the retainer of the exchange catheter to form a looped end section therein.

3. The method according to claim 2, where the retainer is a drawstring and wherein said withdrawing step slidably releases said drawstring from retention around a thinned or tapered end section of said obturator through a shaped aperture in a wall of said drainage catheter.

4. The method according to claim 2 where the retainer is a drawstring and wherein said withdrawing step releases said drawstring by cutting said drawstring with a cutting edge integral to said obturator.

5. The method according to claim 1 further comprising the step of connecting the exchange catheter system to a coupling exterior of the patient's body to commence drainage of fluid from the body region to be drained.

6. An easy-exchange percutaneous drainage catheter system insertable through a tract into patient's body for drainage of fluids from body regions or organs having blocked natural drainage pathways, comprising:
   a drainage catheter insertable through said tract and having at least one main drainage lumen extending to a distal section within the fluid collection space of the organ to be drained;
   an obturator channel alongside and connected to said main lumen and insertable therewith in said tract, said channel having a distal termination at said distal section; and
   a withdrawable obturator sealingly located within said obturator channel and extending to the distal termination of said obturator channel or the vicinity thereof, means for withdrawing said obturator from said channel, means for replacing said obturator with a guidewire along which an exchange catheter system can be inserted through said tract.

7. The system according to claim 6, further comprising a body-external coupling means at the end of said lumen opposite to the said distal section.

8. The system according to claim 6, further comprising a catheter loop-retaining drawstring for releasably retaining said distal section in looped shape, said drawstring extending through a pathway via said lumen into loop-retaining attachment with said lumen at said distal section, means for actuating release of said drawstring when said obturator is withdrawn from said channel.

9. The system according to claim 8, wherein said drawstring release actuating means comprises a release actuating linkage.

10. The system according to claim 8, wherein said obturator withdrawal from said obturator channel actuates the release of said loop-retaining drawstring from its loop-retaining position by slidable release of said drawstring from attachment around an end section of said obturator through a shaped aperture in a wall of said drainage catheter.

11. The system according to claim 8, wherein said obturator withdrawal from said obturator channel actuates the release of said loop-retaining drawstring from its loop-retaining position by a cut through said drawstring with a cutter edge integral to said obturator.

12. The system according to claim 8, wherein said obturator withdrawal from said obturator channel provides an unobturated channel for insertion of a guidewire along and through said unobturated channel into a position within the organ to be drained.

13. The system according to claim 12, further comprising means for maintaining the position of said inserted guidewire during removal of said drainage catheter along said guidewire, and subsequent to said removal.

14. The system according to claim 13, wherein means are provided for installation of said exchange drainage catheter for fluid drainage by guidewire pull-out, catheter-loop formation and loop retention and by body-external connection to a drain collector.

15. The system according to claim 8, wherein said drawstring pathway includes a contoured aperture in a wall section of said catheter.

16. The system according to claim 15, wherein said contoured aperture is the exit aperture for a guidewire near the distal end of said obturator channel.

17. The system according to claim 8, wherein said obturator has embedded throughout a substantial portion of its length a tensile strength-enhancing material.

18. The system according to claim 8, wherein said lumen has a wall and said channel has a wall integral with the wall of said lumen from said distal section to a location outside the patient's body, thereby facilitating insertion and removal of said lumen and channel as a unit along said tract.

19. The system according to claim 8, further comprising body-external connecting means of said main drainage lumen to a drain line with associated drain bag and of said obturator to a handle.

* * * * *